(12) United States Patent
Folsom

(10) Patent No.: US 8,709,045 B1
(45) Date of Patent: Apr. 29, 2014

(54) JOINT FUSING SYSTEM

(76) Inventor: A. Clint Folsom, Pelham, AL (US)

( * ) Notice: Subject to any disclaimer, the term of this patent is extended or adjusted under 35 U.S.C. 154(b) by 63 days.

(21) Appl. No.: 12/749,218

(22) Filed: Mar. 29, 2010

Related U.S. Application Data

(60) Provisional application No. 61/163,964, filed on Mar. 27, 2009.

(51) Int. Cl.
*A61B 17/00* (2006.01)
*A61B 17/70* (2006.01)

(52) U.S. Cl.
USPC ............................................. 606/247; 606/80

(58) Field of Classification Search
USPC .................................................. 606/80, 247
See application file for complete search history.

(56) References Cited

U.S. PATENT DOCUMENTS

| | | | |
|---|---|---|---|
| 5,445,639 A * | 8/1995 | Kuslich et al. | 606/80 |
| 2001/0020186 A1 * | 9/2001 | Boyce et al. | 623/17.16 |
| 2006/0111782 A1 | 5/2006 | Petersen | |
| 2007/0050028 A1 * | 3/2007 | Conner | 623/17.11 |

* cited by examiner

*Primary Examiner* — Sameh Boles
(74) *Attorney, Agent, or Firm* — C. Brandon Browning; Maynard, Cooper & Gale, PC

(57) ABSTRACT

A surgical reamer for cutting an opening in a facet joint for placement of a dowel between the sides of the facet joint to immobilize the joint and create a fusion. The reamer is used with a set of surgical instruments to prepare facet joints for insertion of dowels. The reamer creates a bone shelf above the opening for the dowel to prevent migration of the dowel. The reamer is configured with a flat profile in one plane to allow insertion into the facet joint and the profile of the dowel in the perpendicular plane to create a shape corresponding to the dowel when rotated. The neck of the reamer is smaller in diameter at the coronal end to allow creation of a bone shelf in the facet above the opening for the dowel. The bone shelf resists migration of the dowel out of the prepared opening in the facet.

18 Claims, 9 Drawing Sheets

JOINT FUSING SYSTEM

This application claims the benefit of filing priority under 35 U.S.C. §119 and 37 C.F.R. §1.78 from U.S. Provisional Application Ser. No. 61/163,964 filed Mar. 27, 2009, for Undercutting Reamer For Use In Facet Joint Fusion. All information disclosed in the prior application is incorporated herein by reference.

FIELD OF INVENTION

The present invention relates to a system for fusing a joint, and more particularly, to a kit and method of using same for fusing a spinal facet joint.

BACKGROUND OF INVENTION

The facet joints in the lumbar region of the spine are a source of lower back pain. These joints are located between each vertebra where they prevent excessive rotational motion of the spine. The facet joint is a protrusion of bone on each side of the vertebra that intersects with a protrusion on the vertebra above and below. The joint has a cartilage capsule that provides a lubricated surface for movement. If the facet joint becomes diseased, a patient often will experience pain.

An effective treatment for facet pain is fusion of the facet joint. The joint is fused by removing the cartilage in the joint and placing a spacer in the joint to immobilize the joint and allow the bone protrusions of the facet joint to grow together. A popular fusion technique utilizes insertion of a dowel in a hole drilled through the fact capsule to immobilize the joint and cause bone to grow across the joint and fuse the vertebras. The dowel may be natural bone or a synthetic material. This technique is usually effective, however in some instances the dowel migrates out of the drilled hole before the bones grow together and fuse. This problem occurs because the hole drilled between the two sides of the facet joint is smooth and there is no feature to retain the dowel. If the dowel migrates out of the drilled hole, the surgical procedure must be repeated. Thus, there is a need in the industry to address the aforementioned deficiencies and inadequacies.

SUMMARY OF INVENTION

The present invention is directed to a system for fusing a spinal facet joint. The system comprises a kit including a surgical instrument configured for creating an opening in the facet joint, the opening having an undercut, i.e., a shelf of bone at the superior end of the opening, and a dowel that is configured for insertion into and retention within the opening by expanding the joint. To provide the undercut, the instrument includes a cutter having, in one plane, the same profile as the outer surface of the dowel to be inserted in the opening of the facet joint. In particular, the cutter is flattened in the opposing plane to allow it to be inserted into the facet joint along the plane of the joint and to allow removal of the cutter on the same plane so as to not damage the bone shelf created by the tool. The area above the cutter is narrowed to create the shelf of bone above the dowel to retain the dowel when the two sides of the facet joint move as the patient moves. Thus, after insertion of the dowel into the opening, the joint closes over the dowel and traps the dowel in the opening with the shelf of bone.

DETAILED DESCRIPTION OF PRESENTLY PREFERRED EMBODIMENTS

Figure 1:
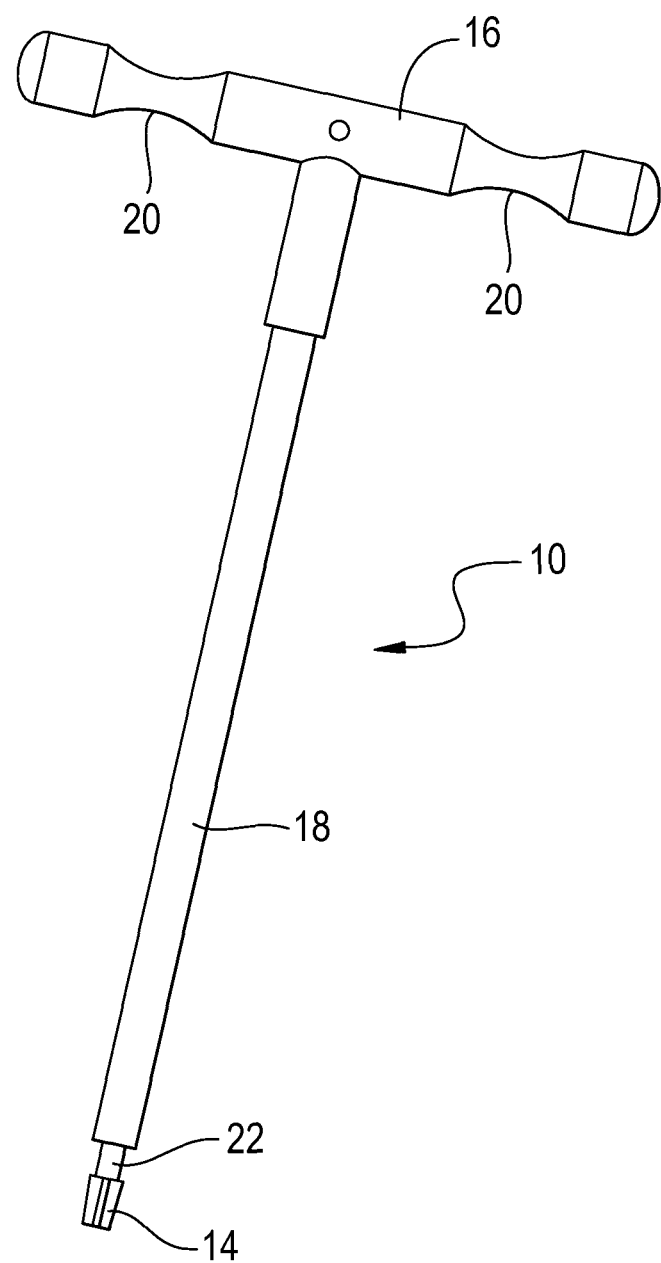
FIG. 1 is a perspective view of a reamer in accordance with a preferred embodiment of the present invention.
Figure 2:
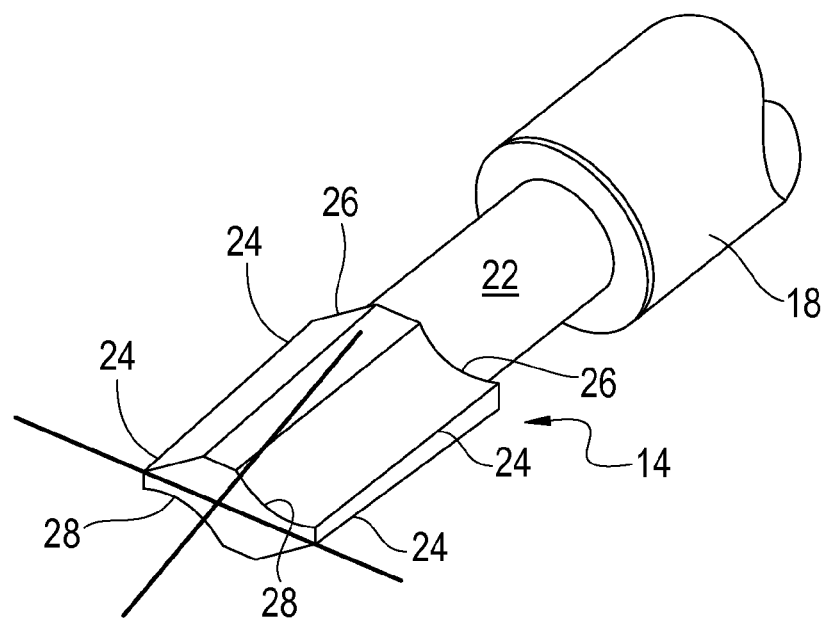
FIG. 2 is a perspective view of the reamer of FIG. 1 illustrating the opposing faces of a cutter head of the reamer.
Figure 3:
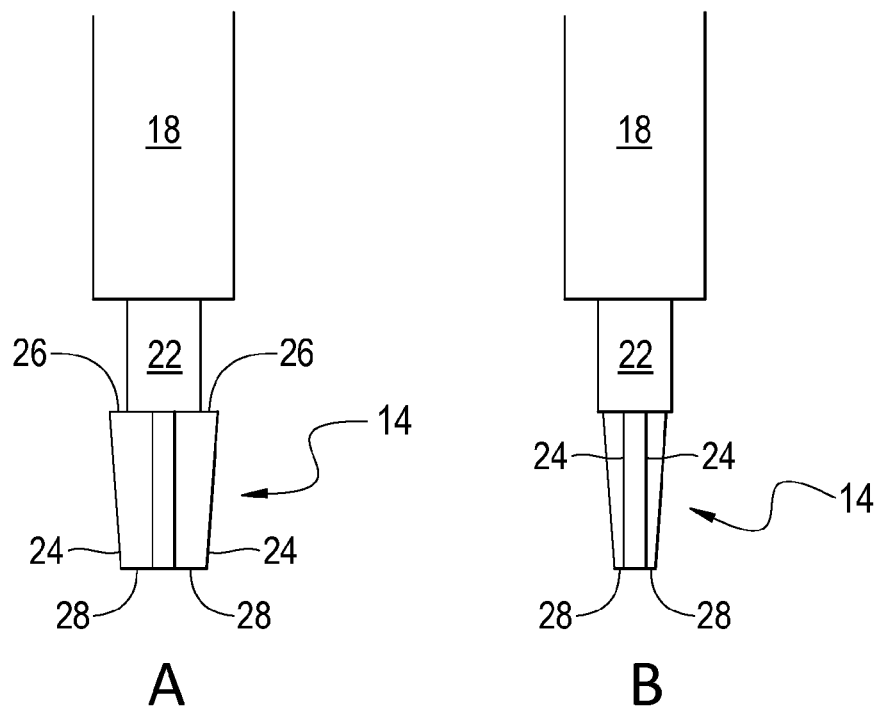
FIG. 3A is a plan view of the cutter head of FIG. 2 illustrating a first cutter plane.
FIG. 3B is plan view of the cutter head of FIG. 2 illustrating a second cutter plane.

FIGS. 1 through 3 depict an undercutting reamer 10 in accordance with a preferred embodiment of the present invention. FIGS. 4 through 9 depict a method for fusing a spinal facet joint 11 using reamer 10 and a bone dowel 12. FIGS. 10 through 13 depict reamers and bone dowels in accordance with other preferred embodiments of the present invention. Generally, reamer 10 includes a cutter 14 configured for sliding into spinal facet joint 11 and forming therein a socket 13 having a sidewall 15, a proximal bone shelf 17 and a distal bone shelf 19. Dowel 12 is configured for being inserted into socket 13 and between shelves 17 and 19 to prevent movement about joint 11.

More particularly, referring to FIG. 1, reamer 10 is composed of a handle 16 and a shaft 18 coupled between handle 16 and cutter 14. Handle 16 is provided for manually rotating shaft 18 and cutter 14. To facilitate rotation of shaft 18 and cutter 14, handle 16 is provided with opposing ergonomic indentations 20 which enable a physician to comfortably grasp and turn handle 16. Coupled between cutter 14 and shaft 18 is a cylindrical neck portion 22 having a diameter that is less than that of dowel 12. The small diameter of neck portion 22 exposes a proximal cutting surface on cutter 14 for allowing the formation of proximal bone shelf 17 upon rotation of cutter 14

Referring to FIG. 2, cutter 14 includes a plurality of cutting edges. These include opposing lateral cutting edges 24, which extend axially to an axis extending through shaft 18, neck 22 and cutter 14, and proximal cutting edges 26 and distal cutting edges 28, which edges 26 and 28 extend radially away from the axis. As explained in more detail hereafter, lateral cutting edges 24 are arranged to form sidewall 15 of socket 13 in joint 11, proximal cutting edges are arranged to form proximal shelf 17 and distal cutting edges 28 are arranged to form distal shelf 19.

Figure 4:
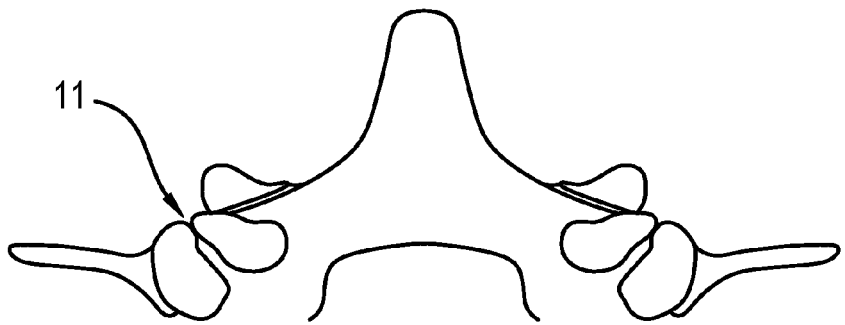
FIG. 4 is a sectional view of a spinal facet joint.
Figure 5:
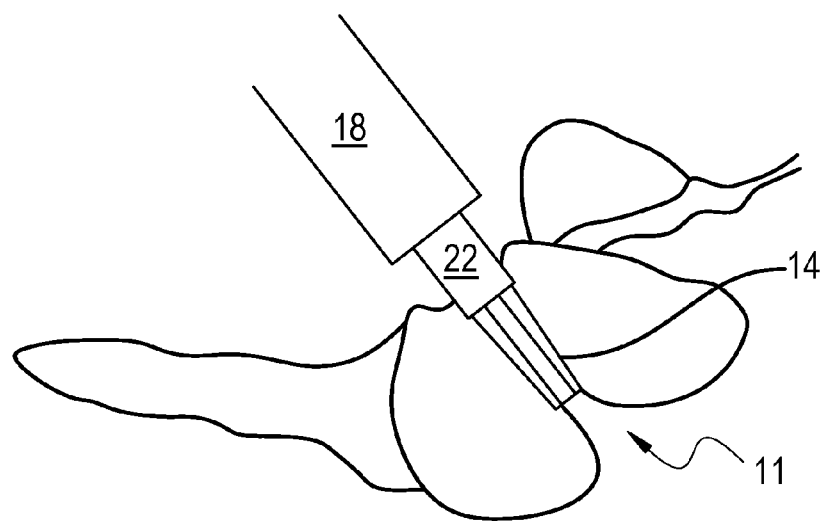
FIG. 5 is a partial sectional view of a spinal facet joint with a cutter head of the reamer of FIG. 1 being inserted into the joint.

Referring to FIG. 3A, the planar geometry of the cutter 14 is depicted with cutter 14 arranged to illustrate a cutter 14 profile defined by opposing lateral cutting edges 24. This profile defines the diameter of socket 13 which is equal to the distance between opposing lateral cutting edges 24. The flat plane of the cutter 14 is illustrated in FIG. 3B by rotating cutter 90 degrees from the arrangement depicted in FIG. 3A. The resulting narrow profile facilitates insertion of cutter 14 between the two opposing surfaces of bone in facet joint 11. In particular, as depicted in FIGS. 4 and 5, the narrow profile of cutter 14 allows for the insertion of cutter 14 into joint 11 without joint 11 having to be substantially expanded to accommodate the cutter. This is accomplished by arranging cutter 14 so that the opposing flat surfaces of cutter 14, which extend between opposing lateral cutting edges 24, are positioned adjacent to the two opposing bony surfaces of joint 11. Once cutter 14 is inserted a distance within joint 11 sufficient to ensure that proximal cutting edges 26, in conjunction with lateral cutting edges 24, can form proximal shelf 17 when rotated, socket 15 is ready to be formed and cutter 14 is rotated.

Figure 6:
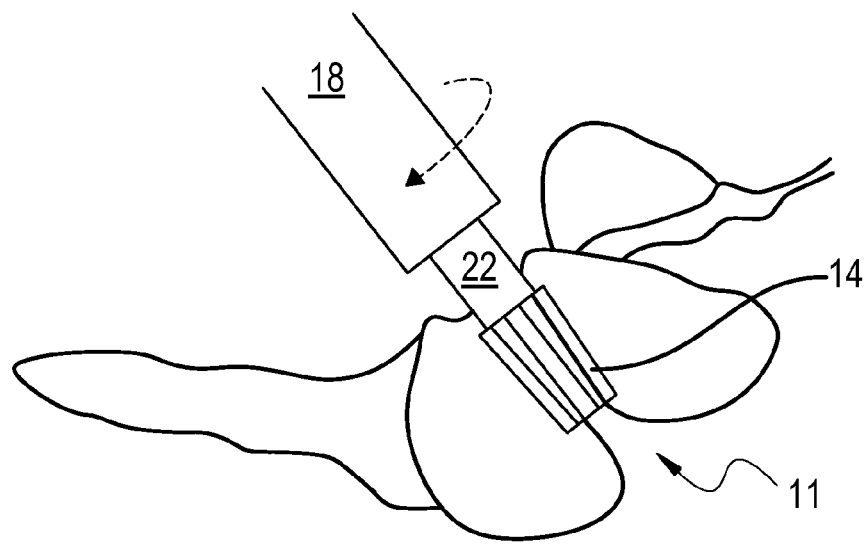
FIG. 6 is a partial sectional view of the spinal facet joint and cutter head of FIG. 5 illustrating the cutting of a socket within the joint.
Figure 7:
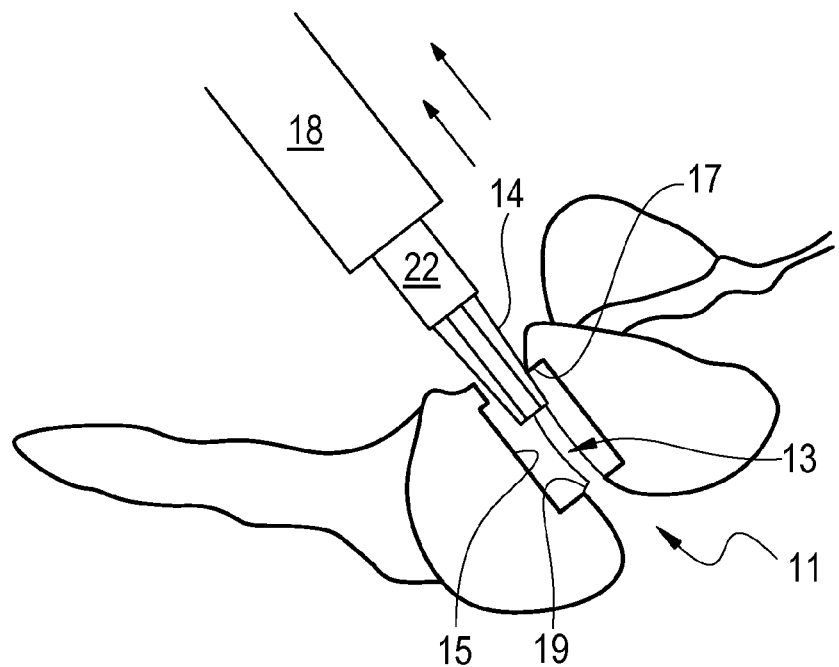
FIG. 7 is a partial sectional view of the spinal facet joint and cutter head of FIG. 6 illustrating removal of the cutter head from the joint.
Figure 8:
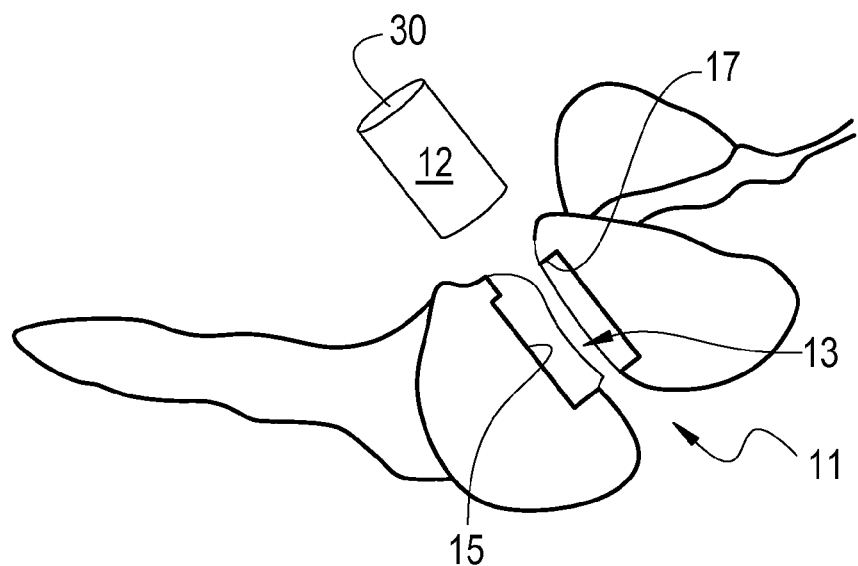
FIG. 8 is a partial sectional view of the spinal facet joint and socket of FIG. 7 illustrating a dowel prior to its insertion into the socket.
Figure 9:
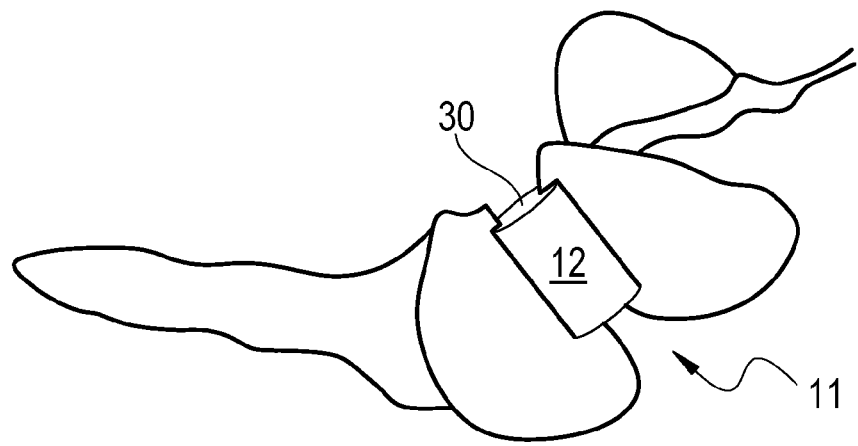
FIG. 9 is a partial sectional view of the spinal facet joint and dowel of FIG. 8 illustrating the arrangement of the dowel within the socket.
Figure 10:
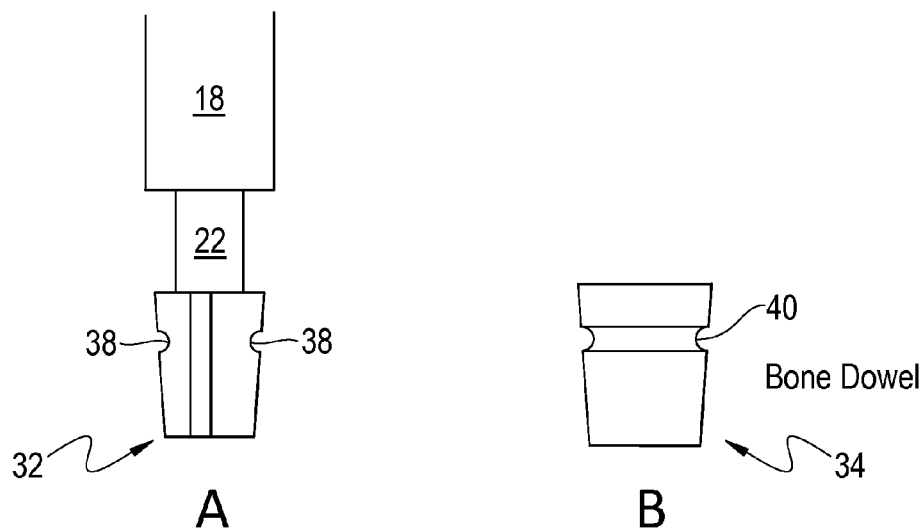
FIG. 10A is a plan view of a cutter head of a reamer in accordance with another preferred embodiment of the invention.
FIG. 10B is a plan view of a dowel configured for use in a spinal facet joint that has been reamed using the cutter head of FIG. 10A.
Figure 11:
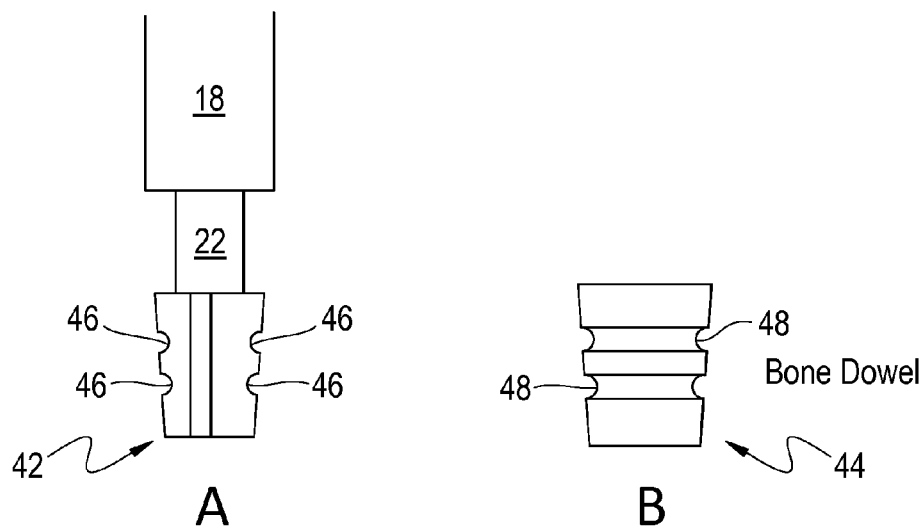
FIG. 11A is a plan view of a cutter head of a reamer in accordance with another preferred embodiment of the invention.
FIG. 11B is a plan view of a dowel configured for use in a spinal facet joint that has been reamed using the cutter head of FIG. 11A.

FIG. 6 depicts rotation of cutter 14 90 degrees from its position illustrated in FIG. 5. In this arrangement, socket 13 can be seen to take on the shape of cutter 14 with socket 13 having a diameter defined by the distance extending between opposing lateral cutting edges 24 and a height defined by the distance extending between proximal cutting edges 26 and distal cutting edges 28. FIG. 6 further depicts the formation of proximal bone shelf 17 by proximal cutting edges 26 and distal bone shelf 19 by distal cutting edges 28. Thus, upon rotation of cutter 14, the cutting edges of cutter 14 cut away bone and cartilage in joint 13 to form socket 13 having dimensions substantially identical to the cutter 14, and as described hereafter, dowel 12.

Following formation of socket 13, cutter 14 is rotated so that the opposing flat surfaces of cutter 14 are again adjacent to the two opposing bony surfaces of joint 11. In this position, cutter 14 can be easily removed from joint 11 without having to expand the joint. Thus, the planar shape of cutter 14 also allows removal of the cutter along the axis of the facet joint so that the cutter profile does not damage newly formed proximal shelf 17 of bone created above socket 13.

Following formation of socket 13 and removal therefrom of cutter 14, dowel 12 is inserted into socket 13. More particularly, referring to FIGS. 8 and 9, dowel 12 is positioned above socket 13 and adjacent to proximal shelf 17. Dowel 12 is then pressed into joint 11, which causes an expansion of joint 11 to accommodate the passage of the dowel beyond proximal shelf 17. Once a proximal end 30 of dowel 12 passes by proximal shelf 17, socket 15 is allowed to contract thereby trapping dowel 12 axially between proximal shelf 17 and distal shelf 19 and radially within socket sidewall 15. This arrangement prevents the migration of dowel 12 out of socket 13 and joint 11.

To further prevent the migration of dowel 12 out of socket 13, other cutter and dowel embodiments are contemplated. In particular, referring to FIGS. 10A and 10B, there are depicted a cutter 32 and a dowel 34 having complimentary indentations. Specifically, cutter 32 includes a pair of indentations 38 formed in the lateral cutting edges of the cutter. These indentations 38, when used to form a socket in a spinal facet joint, will provide the socket with a sidewall having a single inwardly extending radial projection. Dowel 34 includes a radial indentation 40 configured to mate with the radial projection formed in the sidewall of the socket by pair of indentations 38 in cutter 32. The mating of the radial projection with radial indentation 40 provides additional protection against the migration of dowel 34 from the joint socket.

FIGS. 11A and 11B depict a cutter 42 and a dowel 44 having multiple complementary indentions. In particular, cutter 42 includes a pair of indentations 46 formed in each of the opposing lateral cutting edges of the cutter. These indentations 46, when used to form a socket in a spinal facet joint, will provide the socket with a sidewall having two inwardly extending radial projections. Dowel 44 includes a pair of radial indentations 40 configured to mate with the radial projections formed in the sidewall of the socket by pair of indentations 46 in cutter 42.

FIGS. 12A and 12B depict a cutter 50 and a dowel 52 having complimentary projections. Specifically, cutter 50 includes a pair of projections 54 extending from the lateral cutting edges of the cutter. These projections 54, when used to form a socket in a spinal facet joint, will provide the socket with a sidewall having a single outwardly extending radial indentation. Dowel 52 includes a radial projection 56 configured to mate with the radial indentation formed in the sidewall of the socket by pair of projections 54 in cutter 50. The mating of the radial indentation with radial projection 56 provides additional protection against the migration of dowel 52 from the joint socket.

FIGS. 13A and 13B depict a cutter 50 and a dowel 52 having pairs of complimentary projections. Specifically, cutter 58 includes a pair of projections 62 extending from each of the opposing lateral cutting edges of the cutter. These projections 62, when used to form a socket in a spinal facet joint, will provide the socket with a sidewall having a pair of outwardly extending radial indentations. Dowel 60 includes a pair of radial projections 64 configured to mate with the radial indentations formed in the sidewall of the socket by pairs of projections 62 in cutter 58.

Figure 12:
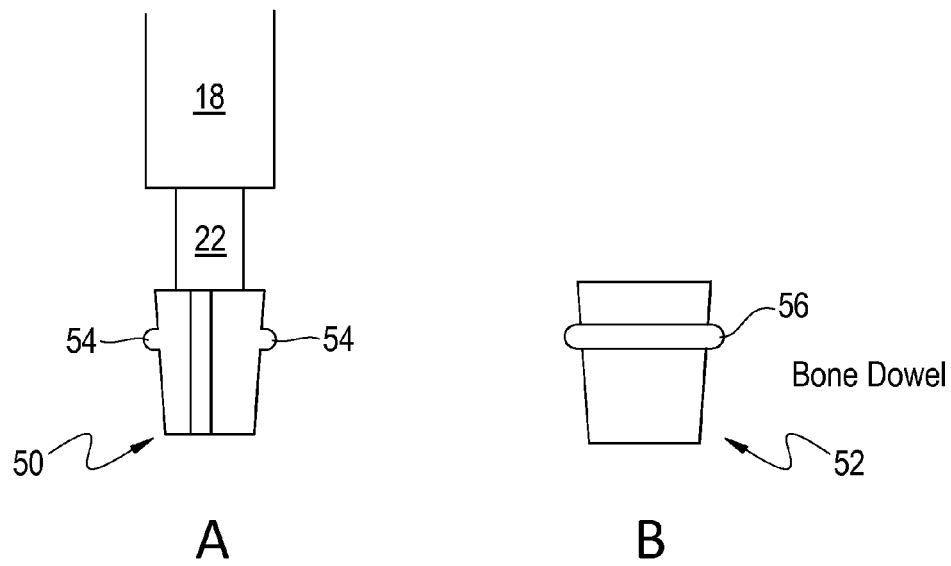
FIG. 12A is a plan view of a cutter head of a reamer in accordance with another preferred embodiment of the invention.
FIG. 12B is a plan view of a dowel configured for use in a spinal facet joint that has been reamed using the cutter head of FIG. 12A.
Figure 13:
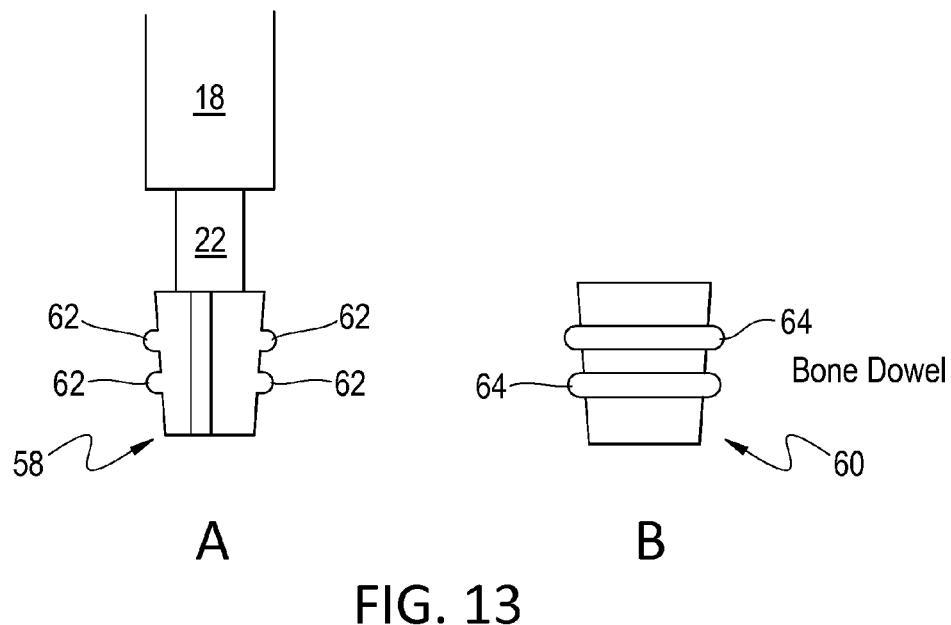
FIG. 13A is a plan view of a cutter head of a reamer in accordance with another preferred embodiment of the invention.
FIG. 13B is a plan view of a dowel configured for use in a spinal facet joint that has been reamed using the cutter head of FIG. 13A.
Figure 14:
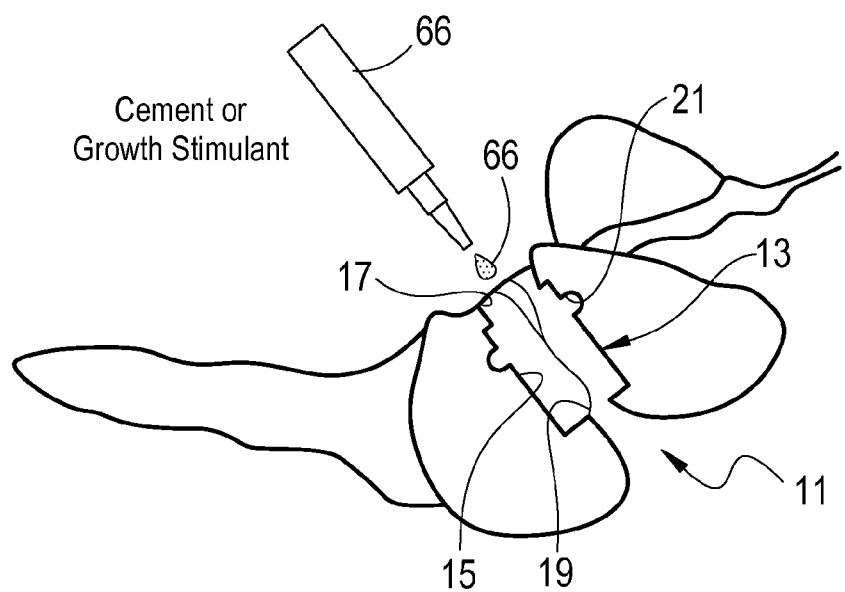
FIG. 14 is a partial sectional view of a spinal facet joint that has been reamed using the cutter head depicted in FIG. 12 illustrating the introduction of a cement or a bone growth stimulant into the socket formed by the cutter head.
Figure 15:
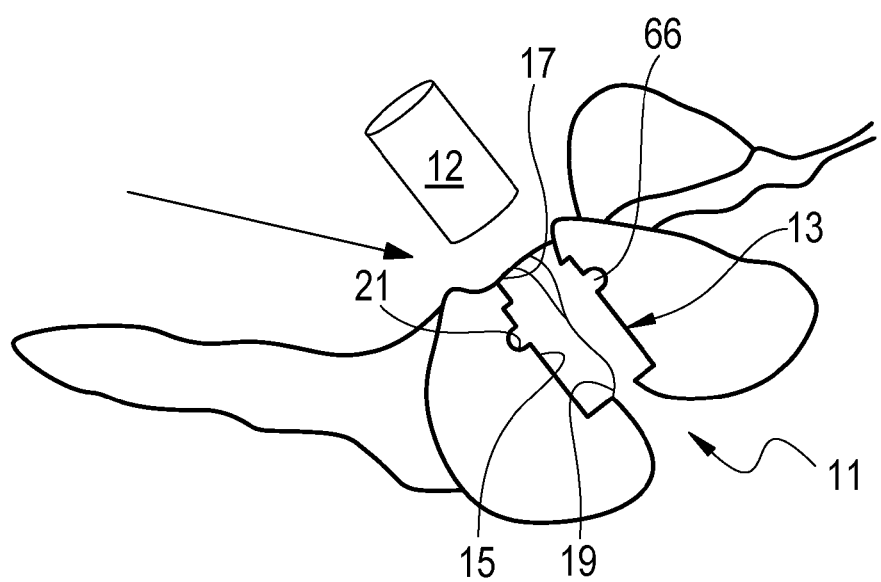
FIG. 15 is a partial sectional view of the facet joint of FIG. 14 illustrating a dowel is to be inserted into the socket.

FIG. 14 depicts a socket 15 formed in a spinal facet joint 11 using cutter 50 of FIG. 12. Socket 15 includes a radial indentation 21 created by projections 54 of the lateral cutting edges of cutter 50. In this embodiment, rather than utilize radial indentation 21 for mating with a radial projection in a dowel, it is contemplated that the radial indentation can be used to receive bone cement or a biologically active bone growth stimulant 66. In particular, cement or growth stimulant 66 can be added to socket 15 followed by insertion of dowel 12 into the socket. Upon insertion of dowel 12 into socket 15, cement or bone growth stimulant 66 migrates into radial indentation 21 where it encircles dowel 12 for aiding in fixing dowel 12 within socket 15. Thus, the radial indentation acts as a reservoir for containing the cement or stimulant and increasing the amount of dowel surface area that is contact with the cement or stimulant.

The surgical procedure for fusing a spinal facet joint using a kit comprised of reamer 10, one or more of cutters 14, 32, 42, 50 and 58 and a plurality of dowels 12, 34, 44, 52 and 60 may be a minimally invasive technique or an open surgical technique. The term minimally invasive or percutaneous refers to performing the surgical operation through a portal placed through the skin and tissue to allow access to the operative site, in this case a spinal facet joint. The advantage of a minimally invasive technique is less destruction of adjacent tissue around the facet joint, less blood loss and less post operative pain for the patient. Recovery times are shorter and time in the hospital and away from normal activities is reduced. Open techniques are performed by making an incision that provides access to the facet joint. An open procedure is indicated if other procedures are to be performed in conjunction with the facet fusion such as reduction of a bulging disc. Open procedures give the surgeon a better understanding of the patient's unique anatomical conditions which may not be visible with imaging equipment. Thus, the surgeon is also able to evaluate the other options to treat the patient more effectively.

In the minimally invasive technique a reamer is inserted into a facet joint through an arthroscopic portal. The reamer is then rotated to produce a socket having an upper and a lower bone shelf. A dowel is inserted into the socket by spreading the joint to allow passage of the dowel. Thereafter, the joint is allowed to close over the dowel. The preferred embodiments of this invention allow use of a dowel with features both protrusive and indented to aid in retention of the dowel in the socket. The preferred embodiments of this invention further allow use of bone cement and growth factors to be placed within radial socket indentations adjacent to the dowel.

It is well established that fusion of the facet joint minimizes pain when performed in conjunction with other surgical procedures done to correct problems with the spine. The fusion of facet joints utilizing the current invention is usually done on both facet joints at a particular level in the spine. However in some cases the facet fusion method described herein may be used on a single site and conventional spine fixation screws used on the other side. Additionally, the fusion of spinal facet joints utilizing the current invention may be applied in combination with an anterior fusion of the vertebral body. This procedure can be done as an open or minimally invasive procedure at the discretion of the surgeon. The fusion of facet joints utilizing the current invention may also be applied in combination with a lamina reduction which is an open procedure.

Modifications and other embodiments of the invention will be apparent to those skilled in the art to which this invention relates having the benefit of the foregoing teachings, descriptions and drawings the present invention is not limited to the specific embodiments disclosed, but is to include modifications and other embodiments which are within the scope of the appended claims.

It is claimed:

1. A method for fusing a facet joint formed by a first protrusion of bone extending from a first vertebra and a second protrusion of bone extending from a second vertebra, the method comprising, forming between the first protrusion and the second protrusion within the facet joint a socket having a sidewall and a shelf at each end of the sidewall extending radially inward, the socket being formed by removing a portion of a joint material, the joint material being selected from the group consisting of cartilage, bone and combinations thereof, and placing a dowel between the shelves thereby immobilizing the facet joint, wherein the socket does not extend into a vertebral body.

2. The method according to claim 1 further comprising expanding the socket, inserting a dowel into the socket, allowing the socket to contract and locking the dowel between the shelves.

3. The method according to claim 1 wherein the joint material is removed by providing a cutter head coupled to a shaft section having a diameter that is less than of the socket, inserting the cutter head and shaft section into the joint, and rotating the cutter head and shaft.

4. The method according to claim 1 further comprising providing a cutter head having a lower radially extending cutting edge, an upper radially extending cutting edge and at least one axially extending cutting edge, inserting the cutter head into the joint, and rotating the cutter head whereby the upper radially extending cutting edge forms one of the shelves, the lower radially extending cutting edge forms the other shelf and the at least one axially extending cutting edge forms the sidewall.

5. A method for fusing a facet joint formed by a first protrusion of bone extending from a first vertebra and a second protrusion of bone extending from a second vertebra, the method comprising, providing a cutter head having a lower radially extending cutting edge, an upper radially extending cutting edge, a first cutting edge extending axially to a cutter head axis, a second cutting edge extending axially to the cutter head axis, a first length extending between the first and the second cutting edges and a second length extending between the upper and the lower cutting edges, inserting the cutter head between the first protrusion and the second protrusion and into the facet joint without substantially expanding the facet joint to accommodate the cutter head, rotating the cutter head, engaging the lower, the upper, the first and the second cutting edges with a joint material selected from the group consisting of cartilage, bone and combinations thereof, cutting away a portion of the joint material without engaging the cutter head with a vertebral body, forming a socket sidewall by cutting away the joint material with the first and second cutting edges, forming an upper socket shelf by cutting away the joint material with the upper cutting edge and forming a lower socket shelf by cutting away the joint material with the lower cutting edge, and positioning the dowel between the upper socket shelf and the lower socket shelf.

6. The method according to claim 5 further comprising inserting into the facet joint along with the cutter head a shaft section having a diameter that is shorter than the first length and rotating the shaft section to thereby rotate the cutter head.

7. The method according to claim 5 further comprising spreading the socket sidewall apart, followed by placing the dowel adjacent to the socket sidewall, followed by contracting the socket sidewall and positioning the dowel between the upper socket shelf and the lower socket shelf.

8. The method according to claim 5 further comprising forming within the facet joint a socket having a diameter that is essentially equal to the first length and a height that is essentially equal to the second length.

9. A method for fusing a facet joint formed by a first protrusion of bone extending from a first vertebra and a second protrusion of bone extending from a second vertebra, the method comprising,
removing from between the first protrusion and the second protrusion a portion of a joint material from the facet joint thereby forming between the first protrusion and the second protrusion and within the facet joint a socket having a sidewall, a bottom wall extending radially inward from a bottom end of the sidewall, and an top wall extending radially inward from a top end of the sidewall, the top wall forming an overhang, and
inserting the dowel between the bottom wall and the overhang and thereby immobilizing the facet joint,
wherein the socket does not extend into a vertebral body.

10. The method according to claim 9 further comprising inserting a cutting head into the facet joint without substantially expanding the facet joint.

11. The method according to claim 10 further comprising inserting a cutting head into the facet joint, the cutting head terminating at a lower end thereof in a first cutting edge, wherein the first cutting edge extends radially inward at and forms the bottom wall.

12. The method according to claim 11 wherein the cutting head terminates at an upper end thereof in a second cutting edge, the second cutting edge extending radially inward and forming the top wall.

13. The method according to claim 10 further comprising inserting a cutting head of a cutting tool into the facet joint, the cutting head terminating at an upper end thereof in a radially extending cutting edge that does not slope inwardly toward an upper end of the cutting tool and wherein the cutting edge forms the top wall.

14. The method according to claim 9 further comprising an edge formed by an intersection of the sidewall and the top wall.

15. The method according to claim 14 wherein the edge includes an angle of about 90 degrees.

16. The method according to claim 9 wherein the overhang is disk-shaped.

17. The method according to claim 9 wherein the bottom wall and the top wall are arranged parallel to one another.

18. The method according to claim 9 wherein the dowel is contained entirely between the bottom wall and the overhang.

* * * * *